United States Patent [19]

Choi

[11] Patent Number: 6,046,305
[45] Date of Patent: Apr. 4, 2000

[54] HETEROFUNCTIONALIZED STAR-SHAPED POLY(ETHYLENE GYCOLS) FOR PROTEIN MODIFICATION

[75] Inventor: Young Kweon Choi, Taejeon, Rep. of Korea

[73] Assignee: MacroMed, Inc., Salt Lake City, Utah

[21] Appl. No.: 09/209,630

[22] Filed: Dec. 11, 1998

Related U.S. Application Data

[60] Provisional application No. 60/069,525, Dec. 12, 1997.

[51] Int. Cl.$^7$ .......................................................... C08F 6/00
[52] U.S. Cl. .......................... 528/491; 528/486; 528/495; 528/502 R; 530/815; 514/2
[58] Field of Search ..................................... 528/486, 491, 528/495, 502 R; 530/815; 514/2

[56] References Cited

PUBLICATIONS

Koji Yoshinga and J. Milton Harris, Effects of Coupling Chemistry on the Activity of Poly(ethylene glycol)–Modified Alkaline Phosphatase, pp. 17 to 24.

Katre et al., Proc. Natl. Acad. Sci. USA 84 pp. 1487 (1987).

Chiu et al., Bioconjugate Chem. 4 pp. 290 (1993).

Clark et al., J. Biol. Chem. 271 pp. 21969–21977 (1996).

Inada et al., Meth. Enzymology 242 pp. 65–90 (1994).

Biotechnol. Appl. Biochem. 17 pp. 115–130 (1993).

Fuke et al., J. Controlled Release 30 pp. 27–34 (1994).

Sasaki et al., Biochem. Biophys. Res. Chem. 197 pp. 287–291.

Kodera et al., Bioconjugate Chem. 5 pp. 283–286 (1994).

*Primary Examiner*—Duc Truong
*Attorney, Agent, or Firm*—Thorpe North & Western LLP

[57] ABSTRACT

A biocompatible, heterofunctional, star-shaped poly (ethylene glycol) is described. Methods of making the heterofunctional star-shaped poly(ethylene glycol) and using it for conjugation with proteins are also described.

18 Claims, No Drawings

HETEROFUNCTIONALIZED STAR-SHAPED POLY(ETHYLENE GYCOLS) FOR PROTEIN MODIFICATION

CROSS-REFERENCE TO RELATED APPLICATIONS

This application claims the benefit of U.S. Provisional Application No. 60/069,525, filed Dec. 12, 1997.

BACKGROUND OF THE INVENTION

This invention relates to heterofunctionalized star-shaped poly(ethylene glycols) (PEGs) and a methods of making and using thereof. More particularly, the invention relates to star-shaped PEGs having an amine, carboxyl, aldehyde, thiol, halogen, or epoxide group on an end thereof, which allows reaction with proteins or other molecules.

Recently, much attention has been paid to peptides and proteins as drugs due to the development of recombinant DNA technology and the corresponding ease of making such peptides and proteins. Cytokines and biological response modifiers, thrombolytics, adhesion molecules, and agonist and antagonist peptide fragments of growth factors, all have wide-spread applications. From the pharmaceutical point of view, however, these drugs have several limitations such as short half-life, low stability to proteolytic digestion, and immunological side effects ranging from mild allergic reactions to anaphylactic shock. Chemical modification of a protein drug by a polymer is one of the current strategies to diminish these limitations. Poly(ethylene glycol) has been most extensively used as chemical modifying agent due to its non-toxic, non-immunogenic, and amphipathic properties. PEG has been approved by the FDA for internal use. Over 40 proteins have now been modified with PEG, including asparaginase, glutaminase, uricase, superoxide dismutase, lactoferrin, streptokinase, plasmin-streptokinase complex, adenosine deaminase, interleukin-2, N. V. Katre et al., 84 Proc. Nat'l Acad. Sci. USA 1487 (1987); catalase, arginase, insulin, b-glucuronidase, trypsin, chymotrypsin, J. Kopecek et al., 4 Bioconjugate Chem. 290 (1993); hemoglobin, recombinant human granulocyte colony stimulating factor (rhG-CSF), and recombinant human growth hormone (rhGH), R. Clark et al., 271 J. Biol. Chem. 21969–21977 (1996). Presently, asparaginase modified with monomethoxy PEG is approved by the FDA for use in patients with immunological reaction to the free enzyme.

It is well known that chemical modification by PEG almost invariably achieves increased biological half-life, reduced antigenicity, and increased resistance to proteolysis. The increased half-life is the most prominent effect of PEG modification, and is explained by several mechanisms, such as the increased size of proteins; interference with interaction of carbohydrate chains with their specific receptors; masking specific sequences for which there are cellular receptors; and reduced proteolysis and antigenicity. The extension of half-life is generally proportional to the number of PEG molecules attached per molecule. The specific activity of the protein generally decreases, however, as the degree of modification increases. The reduction of immunogenicity by PEG modification is clinically significant because life-threatening allergic reaction can be avoided. The mechanism may be via shielding of antigenic determinants by PEG, which is known to be immunologically inert. The PEG modification also protects proteins from attack by proteases and inhibitors. In addition to pharmacokinetic and immunological improvements, it has been reported that solubility in both water and organic solvents and thermal-mechanical stability increase as a result of PEG modification.

The vast majority of PEG-modified proteins, however, show some decrease in bioactivity and undergo denaturation, resulting in deactivation by chemical modification. Therefore, when a protein is chemically modified by PEG, one should carefully select the reaction conditions, as well as the configuration of the PEG molecule, so as to maximize the modification effect and minimize the protein deactivation. Due to well-established advantages of PEG modification, coupling technology regarding reaction conditions and molecular weights of PEG has been studied and reported in the literature. J. M. Harris, Poly(ethylene glycol) Chemistry: Biotechnical Biomedical Applications (1992); Y. Inada et al., 242 Meth. Enzymology 65–90 (1994); 17 Biotechnol. Appl. Biochem. 115–130 (1993); K. Yoshinga et al., 4 Bioactive Biocompatible Polymer 17–24 (1989). However, most studies to date are restricted to the modification using linear PEGs. More recently, new types of PEGs have been explored for protein modification. One-, two-, and three-branched PEG derivatives, each having only one carboxyl group in a molecule, have been obtained by reacting monomethoxy linear PEG with bromoacetic acid, protocatechnic acid, and gallic acid, respectively. I. Fuke, et al., 30 J. Controlled Release 27–34 (1994). It was found that trypsin modified with a branched PEG was greatly protected from pepsin digestion, with the degree of protection corresponding directly to the number of branches. Asparaginase modified with a two-branched PEG was obtained by reaction of monomethoxy PEG 5000 with two chlorines of trichlorotriazine. It has been shown that modification of asparaginase by a branched PEG resulted in an increase of in vivo activity, proteolytic resistance, stability, and half-life. However, these branched PEGs have been prepared by a coupling reaction using linear PEGs and multifunctional core compounds, which is cumbersome and difficult for obtaining branched PEG in high yields and purity. In addition, such a coupling process does not yield branched PEGs with a higher number of arms. Another disadvantage is that branched PEGs obtained from the coupling process have reactive functional groups interior of the PEG molecule, rendering the conjugation between the branched PEG and a protein less efficient than would be desired. Comb-shaped polyethylene oxide (PEO) has also been prepared and conjugated with bovine serum albumin and asparaginase for reducing immunogenicity. H. Sasaki et al., 197 Biochem. Biophys. Res. Chem. 287–291 (1993); Y. Kodera et al., 5 Bioconjugate Chem. 283–286 (1994).

The present invention relates to a method for making a star-shaped PEG. Star-shaped polymers comprise several linear chains linked together at one end of each chain, constituting the simplest form of branching. There exist two distinct synthetic approaches for star-shaped polymers: divergent and convergent approaches. The convergent approach, called the "arm-first method," involves the termination of growing polymer chains with multifunctional terminating agents to form the star-shaped polymer. The convergent method combined with anionic living polymerization, a newly developed technique, is known to produce a star-shaped polymer of controlled arm length, narrow molecular weight distribution, and easily varied arm number. The most common method for the synthesis of this type of polymer has involved homogeneous organolithium polymerization, followed by a linking reaction between the lithium chain end and the linking agents, such as chlorosilanes, phthalate esters, and m- and p-divinyl benzenes. The main drawback of this method is that the branches of star-shaped molecules cannot be modified with functional groups at their outer ends.

The divergent approach, also called the "core-first method," starts the synthesis reaction from a plurifunctional initiator and proceeds outward. This technique allows the modification of the branches with functional groups at their outer ends, thus providing the possibility of further reaction for forming block copolymers or selective adsorption. A problem associated with this method is the poor solubility of plurifunctional organometallic initiators, even in polar solvents. Due to its simplicity, the divergent method has been commonly applied for a variety of star-shaped gellation can happen due to a crosslinking reaction because proteins, in general, have several accessible amino groups.

In view of the foregoing, it will be appreciated that providing a heterofunctionalized star-shaped PEG and method of making thereof would be a significant advancement in the art.

BRIEF SUMMARY OF THE INVENTION

It is an object of the present invention to provide a star-shaped PEG bearing heterofunctional end groups and a method of making thereof.

It is another object of the invention to provide an improved method of making star-shaped PEGs.

These and other objects can be addressed by providing a biocompatible, heterofunctional, star-shaped poly(ethylene glycol) represented by the formula:

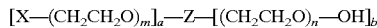

wherein X is amine, carboxyl, aldehyde, thiol, halogen, or epoxide; Z represents amide, carbamate, or ester bonds; m and n are integers ranging from about 10 to 2,000; a is an integer from about 1 to 5; and b is an integer from about 1 to 100.

A method of making a biocompatible, heterofunctional, star-shaped poly(ethylene glycol) comprises:

(a) synthesizing a first poly(ethylene glycol) arm containing an allyl end group by ring opening polymerization of ethylene oxide initiated with a metal salt of an alkenol;

(b) terminating synthesis of the first poly(ethylene glycol) arm by reaction with acid to result in a hydroxy terminal group;

(c) activating the hydroxy terminal group by reaction with a polyfunctional compound containing a plurality of hydroxyl groups;

(d) synthesizing a plurality of branch poly(ethylene glycol) arms by ethylene oxide polymerization, wherein each of the plurality of branch poly(ethylene glycol) arms is bonded to one of the plurality of hydroxyl groups, resulting in the heterofunctional, star-shaped poly(ethylene glycol) containing an allyl end group.

DETAILED DESCRIPTION

Before the present composition and method for heterofunctionalized star-shaped poly(ethylene glycols) are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise.

In describing and claiming the present invention, the following terminology will be used in accordance with the definitions set out herein.

As used herein, "peptide" means peptides of any length and includes proteins. The terms "polypeptide" and "oligopeptide" are used herein without any particular intended size limitation, unless a particular size is otherwise stated. Typical of peptides that can be utilized are those selected from group consisting of oxytocin, vasopressin, adrenocorticotrophic hormone, epidermal growth factor, prolactin, luliberin or luteinising hormone releasing hormone, growth hormone, growth hormone releasing factor, insulin, somatostatin, glucagon, interferon, gastrin, tetragastrin, pentagastrin, urogastroine, secretin, calcitonin, enkephalins, endorphins, angiotensins, renin, bradykinin, bacitracins, polymixins, colistins, tyrocidin, gramicidines, and synthetic analogues, modifications and pharmacologically active fragments thereof, monoclonal antibodies and soluble vaccines. The only limitation to the peptide or protein that may be utilized is one of functionality.

The present invention relates to a star-shaped polymer bearing heterofunctional end groups and their use to modify proteins for improved pharmacokinetic, pharmacological, and immunological properties. The synthesis of the heterofunctional star-shaped PEG is based on a "one-arm-first method," which is basically an improvement of the "arm-first method" and the "core-first method." In this method, one arm bearing a functional group is prepared first by ring-opening polymerization of ethylene oxide initiated with a heterobifunctional compound, and then the growing polymer chain end is terminated by a polyfunctional compound followed by sequential polymerization of ethylene oxide. In this case, the heterobifunctional initiator for the first arm bears (a) an alkoxide to initiate ethylene oxide and (b) a functional group for protein conjugation. The functional group for protein conjugation needs to be a precursor, which is inert during the course of ethylene oxide polymerization but is subject to being restored to active form. As a result, star-shaped PEGs can be obtained that are heterofunctional, where an end group originated from the first PEG arm can be different from the other PEG arms. Practically, the functional group of the first arm is designed to be of higher chemical reactivity than that of the other arms.

Star-shaped polymers have three-dimensional, hyperbranched structures exhibiting characteristic physical properties due to their unusual architecture. The study of star-shaped polymers of well-defined structure permits a more quantitative study of the effects of branching of one special form. Thus, the synthesis of well-defined star-shaped polymers is of great value. Well-known anionic polymerization techniques allow the synthesis of well-defined polymers in terms of molecular weight, molecular weight distribution, and end group functionalization.

The present invention provides a heterofunctional star-shaped PEG and a method of conjugating to a protein. The heterofunctional star-shaped PEG comprises a central residue derived from a plurifunctional compound having at least 3 hydroxyl groups and a plurality of polymeric branches or arms with an average molecular weight of 500 to 10,000 attached to the hydroxyl group branching locations wherein the polymeric arms are formed of PEG. The end groups of polymer arms are prepared to be heterofunctional, and thus one end group is reactive enough to conjugate to a protein site-specifically while the other end groups are inert or at least must less reactive than the reactive one. The reactive group is selected from the group consisting of amine, carboxyl, aldehyde, thiol, halogen, and epoxide groups, where the carboxyl functional group is the most preferred for the reaction with amino groups of protein.

The synthesis of the heterofunctional star-shaped PEG, called the "one-arm-first method," is begun with the preparation of one PEG arm by ring opening polymerization of ethylene oxide initiated with a metal salt of an alkenol. The alkenol is selected from the group consisting of vinyl alcohol, 2-propen-1-ol (allyl alcohol), 3-buten-1-ol (allylcarbinol), 4-penten-1-ol (2-allylethyl alcohol), 5-hexen-1-ol, 6-hepten-1-ol, and 7-octen-1-ol, and the like. For the anionic polymerization of ethylene oxide, the alkenol is required to be converted to a highly reactive organometallic compound to achieve a fast rate of polymerization. The metal is selected from the group consisting of potassium, sodium, lithium, yttrium, and lanthanide seried rare earth metals, where potassium is preferred as the counter-ion to obtain acceptable polymerization rates at temperatures just above ambient. An alkoxide site is obtained upon reaction of the alkenol with a metal-organic nucleophile, such as fluorenylpotassium, diphenylmethylpotassium, potassium naphthylide, or potassium tert-butoxide, under conditions chosen such as to avoid attack of the unsaturation. The polymerization can be done either in bulk or in solution. The preferred solvents are highly polar, which permits good solvation of the cation and thus promotes the nucleophilicity of the base. Tetrahydrofuran (THF) is most preferred. Suitable reaction temperatures for solution polymerization range from −50 to 150° C., with 20 to 80° C. being the preferred range. The preferred temperatures for the bulk polymerization is 0 to 60° C. The degree of polymerization is generally controlled by the monomer to initiator concentration ratio.

When the polymerization of the first arm is finished, the growing chain end site is terminated with acids such as hydrochloric acid or acetic acid, resulting in an hydroxyl terminal group. The hydroxyl terminal site is end-capped again with a polyfunctional compound for sequential polymerization of ethylene oxide. The polyfunctional compound is selected from compounds containing monoamine and polyhydroxy groups in a same molecule, and thus is preferably selected from the group consisting of polyhydroxyalkylmonoamines, such as tris(hydroxymethyl) aminomethane and aminosugars such as glucosamine, galactosamine, and lactosamine. Various coupling methods can be used for the end-capping process. In one particular embodiment of the present invention, the terminal hydroxyl group is activated with 4-nitrophenyl chloroformate and then coupled with tri(hydroxymethyl)aminomethane, resulting in the α-vinyl-ω-tris(hydroxymethyl) PEG. The ethylene oxide polymerization initiated with a metal salt of a tris (hydroxymethyl) group results in a 4-arm star-shaped PEG, where only one arm has an allyl group at the chain end and the remaining three arms have hydroxyl groups. The polymerization can be done under the same conditions as for the first arm. The individual arm segments generally have a molecular weight of about 500 to 50,000. The total molecular weight of a star-shaped PEG generally will be about 1,000 to 100,000. The molecular weight of the first arm can be either the same or different from the other arms. Due to the characteristics of anionic polymerization applied in the present invention, the number and length of arms are precisely controllable in the wide range.

Once the star-shaped PEG with only one available vinyl group is synthesized, the vinyl group can be directly used for conjugation with a protein or can be converted into other appropriate functional groups, depending on the conjugation conditions. A sulfhydryl-selective reaction is preferred for the direct use of the vinyl group, as shown in Formula 1 below.

(Formula 1)

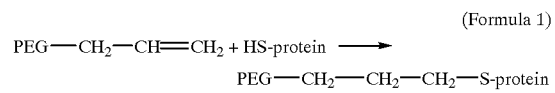

The vinyl group can be further converted into various functional groups, such as amine, carboxyl, aldehyde, thiol, halogen, epoxide, and cyano groups. These conversion reactions are set out in the following formulas.

(Formula 2)

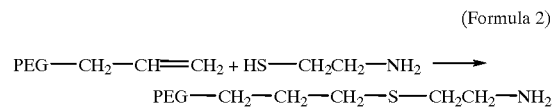

(Formula 3)

(Formula 4)

(Formula 5)

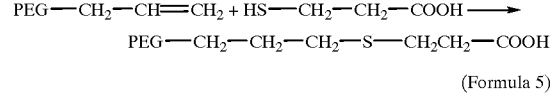

(Formula 6)

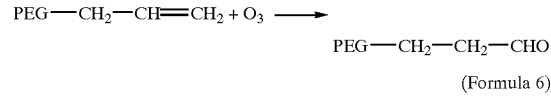

(Formula 7)

PEG—CH$_2$—CH=CH$_2$ + HBr ⟶ PEG—CH$_2$CHBrCH$_3$ (Formula 8)

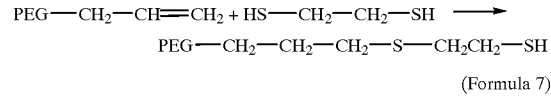

The reaction producing the carboxyl group is preferred for conjugation with amino groups of protein, resulting in an amide linkage, as shown below.

(Formula 9)

The resulting amide linkage can be formed either by direct coupling or after activating a free carboxyl group with a proper activating agent. The direct coupling can be catalyzed by water-soluble carbodiimide, N-(3-dimethylaminopropyl)-N'-ethylcarbodiimide hydrochloride. The free carboxyl group is activated using well-known methods in the art, such as the active ester method or the mixed anhydride method.

In conclusion, the present invention provides a star-shaped PEG for protein modification. It is advantageous to be able to obtain well-defined branched PEGs, which are required for more selective and efficient protein modification. In addition, by changing the number of arms and degree of polymerization in a star-shaped PEG, the most suitable configuration of star-shaped PEG for conjugation with a protein can be selected.

Example 1

In this example the preparation of a 3-arm star-shaped PEG bearing a carboxyl group at an end thereof is described.

Potassium Salt of Allyl Alcohol

The initiator solution was freshly prepared prior to use. One mmole of allyl alcohol was dissolved in dry THF (10 ml), followed by reaction with an equimolar amount of potassium tert-butoxide (1 M in THF; Aldrich, Milwaukee, Wis.) under a nitrogen atmosphere. After adjusting its concentration to 0.1 M by adding dry THF, the solution was directly used for ethylene oxide polymerization without a further isolation procedure.

Synthesis of First PEG Arm

The first PEG arm was synthesized by ethylene oxide (Fluka) polymerization initiated with the potassium salt of allyl alcohol. The polymerization was carried out in THF with stirring in a previously flamed and pre-evacuated reaction flask. Ethylene oxide was first distilled from potassium hydroxide and subsequently distilled from calcium hydride by a trap-to-trap distillation method, in which dry ice-acetone mixture was used for condensation of ethylene oxide. After collecting the predetermined amount (45 mmoles) of ethylene oxide in a graduated cylinder, it was again transferred into the reaction flask by trap-to-trap distillation. The potassium salt of allyl alcohol in THF was then introduced into the reaction flask with a GASTIGHT syringe (Aldrich) under reduced pressure. The ratio of monomer concentration to initiator was 45:1 to yield a PEG of molecular weight of about 2000. The final monomer concentration was adjusted to 2 M by adding freshly dried THF, and then polymerization was carried out for 3 days at 40° C. The polymerization was terminated by adding an excess amount (relative to the initiator) of 1 N HCl solution. The first PEG arm product was precipitated in diethyl ether and was dialyzed against water and freeze dried.

Synthesis of 3-arm Star-shaped PEG

The hydroxyl end group of the first PEG arm, α-allyl-ω-hydroxy PEG 2000, was activated with 4-nitrophenylchloroformate in the presence of triethylamine and then reacted with an equimolar amount of serinol (2-amino-1,3-propanediol) in dimethylformamide. After precipitation in diethylether and purification by dialysis against water, the α-allyl-ω-bis(hydroxymethyl) methylamino PEG 2000 was converted into its corresponding alkoxide using potassium tert-butoxide, and then ethylene oxide polymerization was conducted as described above, except that the concentration ratio of the monomer to the initiator was 90: 1. Product was obtained by precipitation in an excess amount of diethyl ether after acidification with 0.1 N hydrochloric acid.

Modification of Allyl End Group

The allyl end group was modified to a carboxyl group, enabling the conjugation of the star-shaped PEG to a protein. The polymer (1 mmole) was added to a solution of 2-carboxyethanethiol (1.5 mmole) in dimethylformamide. After stirring at room temperature for 5 hours, the product was recovered by precipitation in an excess amount of diethyl ether followed by purification by dialysis against water.

Polymer Characterization

The star-shaped PEG was characterized using gel permeation chromatography (GPC), $^1$H-NMR, and end group titration. GPC was performed using a Waters liquid chromatography system equipped with a Waters 501 pump, 712 WISP autosampler, 745 Data Module, R401 Differential Refractometer, and a set of ULTRASTYRAGEL columns (linear and 500 Å pore size, Waters Co.) and PEO standards (Polysciences Inc.). $^1$H-NMR spectra were recorded using a Bruker AS200 FT spectrometer in DMSO-$d_6$ with tetramethylsilane (TMS) as an internal standard. Hydroxyl termini of PEO exhibited a clean triplet at 4.56 ppm in DMSO-$d_6$. Hydroxyl and carboxylic end groups of PEO derivatives were determined by visual titrimetric methods. In the case of carboxylic groups, samples ($1.50 \times 10^{-3}$ mole each) dissolved in distilled water were titrated against standard aqueous sodium hydroxide solution (0.03 N) using a few drops of 1% phenolphthalein in ethanol as an indicator. The final amount of sodium hydroxide consumed by PEO derivatives gave the information on the number of carboxylic and groups per one molecule of PEO derivatives gave the information on the number of carboxylic end groups per one molecule of PEO derivatives. The hydroxyl groups were titrated as above after converting into carboxylic esters by acylation with an excess amount of acetyl chloride in an organic phase followed by hydrolysis.

Example 2

In this example, a 4-arm star-shaped PEG bearing a carboxyl group at an end thereof was prepared according to the procedure of Example 1 except that the hydroxyl end group of the first PEG arm, α-allyl-ω-hydroxy PEG 2000, was modified with tris(hydroxylmethyl)aminomethane, resulting in the 4-arm star-shaped PEG bearing an amino group at an end. The individual molecular weight of each arm was about 2,000, and thus the total molecular weight was about 8,000.

Example 3

In this example, the preparation of a 4-arm star-shaped PEG bearing a carboxyl group at an end thereof is described. The first PEG arm was end-capped with glucosamine to yield α-allyl-ω-glucosyl PEG 2000. Ethylene oxide polymerization initiated with α-allyl-ω-glucosyl PEG 2000 was conducted in the same way as described in Example 1. After adding freshly distilled ethylene oxide to the trap-to-trap distillation reaction, the reaction flask was incubated for 3 days at 40° C. for polymerization to occur. Termination and isolation were carried out as described above for the 3-arm star-shaped PEG. The reaction yielded a 5-arm star-shaped PEG 10,000 bearing one carboxyl terminal group out of five.

I claim:

1. A biocompatible, heterofunctional, star-shaped poly (ethylene glycol) represented by the formula:

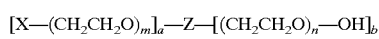

[X—(CH$_2$CH$_2$O)$_m$]$_a$—Z—[(CH$_2$CH$_2$O)$_n$—OH]$_b$ wherein X is amine, carboxyl, aldehyde, thiol, halogen, or epoxide; Z represents amide, carbamate, or ester bonds; m and n are integers ranging from about 10 to 2,000; a is an integer from about 1 to 5; and b is an integer from about 1 to 100.

2. A method of making a biocompatible, heterofunctional, star-shaped poly(ethylene glycol) comprising:
   (a) synthesizing a first poly(ethylene glycol) arm containing an allyl end group by ring opening polymerization of ethylene oxide initiated with a metal salt of an alkenol;

(b) terminating synthesis of the first poly(ethylene glycol) arm by reaction with acid to result in a hydroxy terminal group;

(c) activating said hydroxy terminal group by reaction with a polyfunctional compound containing a plurality of hydroxyl groups;

(d) synthesizing a plurality of branch poly(ethylene glycol) arms by ethylene oxide polymerization, wherein each of said plurality of branch poly(ethylene glycol) arms is bonded to one of said plurality of hydroxyl groups, resulting in the heterofunctional, star-shaped poly(ethylene glycol) containing an allyl end group.

3. The method of claim 2 wherein said alkenol is a member selected from the group consisting of vinyl alcohol, 2-propen-1-ol (allyl alcohol), 3-buten-1-ol (allylcarbinol), 4-penten-1-ol (2-allylethyl alcohol), 5-hexen-1-ol, 6-hepten-1-ol, and 7-octen-1-ol.

4. The method of claim 2 wherein the metal of said metal salt is a member selected from the group consisting of potassium, sodium, lithium, yttrium, and lanthanide.

5. The method of claim 4 wherein said metal is potassium.

6. The method of claim 2 wherein said acid is hydrochloric acid or acetic acid.

7. The method of claim 2 wherein said polyfunctional compound is a member selected from the group consisting of polyhydroxyalkylmonoamines and aminosugars.

8. The method of claim 7 wherein said polyhydroxyalkylmonoamine is tris(hydroxymethyl)amino methane.

9. The method of claim 7 wherein said aminosugar is a member selected from the group consisting of glucosamine, galactosamine, and lactosamine.

10. The method of claim 2 further comprising reacting the allyl end group of the star-shaped poly(ethylene glycol) with a thiol group of an alkyl compound containing terminal thiol and amino groups thereby obtaining a star-shaped poly(ethylene glycol) containing a terminal amino group.

11. The method of claim 2 further comprising reacting the allyl end group of the star-shaped poly(ethylene glycol) with a thiol group of an alkyl compound containing terminal thiol and carboxyl groups thereby obtaining a star-shaped poly(ethylene glycol) containing a terminal carboxyl group.

12. The method of claim 2 further comprising reacting the allyl end group of the star-shaped poly(ethylene glycol) with a thiol group of an alkyl compound containing two terminal thiol groups thereby obtaining a star-shaped poly(ethylene glycol) containing a terminal thiol group.

13. The method of claim 2 further comprising oxidizing the allyl end group of the star-shaped poly(ethylene glycol) with an oxidizing agent selected from the group consisting potassium permangante, osmium tetraoxide and equavalents thereof, thereby obtaining a star-shaped poly(ethylene glycol) containing a terminal carboxyl group.

14. The method of claim 2 further comprising oxidizing the allyl end group of the star-shaped poly(ethylene glycol) with ozone thereby obtaining a star-shaped poly(ethylene glycol) containing a terminal epoxide group.

15. The method of claim 2 further comprising oxidizing the allyl end group of the star-shaped poly(ethylene glycol) with ozone thereby obtaining a star-shaped poly(ethylene glycol) containing a terminal aldehyde group.

16. The method of claim 2 further comprising reacting the allyl end group of the star-shaped poly(ethylene glycol) with a hydrogen halide thereby obtaining a star-shaped poly(ethylene glycol) containing a terminal methyl halogen group.

17. A method for conjugating a protein with a star-shaped poly(ethylene glycol) comprising reacting a protein containing a thiol group with a star-shaped poly(ethylene glycol) containing a terminal allyl group.

18. A method for conjugating a protein with a star-shaped poly(ethylene glycol) comprising reacting a protein containing an amino group with a star-shaped poly(ethylene glycol) containing a terminal carboxyl group.

* * * * *